United States Patent
Ritter et al.

(10) Patent No.: US 12,386,001 B2
(45) Date of Patent: Aug. 12, 2025

(54) ESTIMATING AN INFLUENCE OF A MAGNETIC RESONANCE TOMOGRAPHY SEQUENCE ON AT LEAST ONE COMPONENT IN OR ON AN EXAMINATION TUNNEL AND PROTECTION OF THE COMPONENT

(71) Applicant: Siemens Healthineers AG, Forchheim (DE)

(72) Inventors: Dieter Ritter, Fuerth (DE); Ludwig Eberler, Neumarkt.i.d.OPf. (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 0 days.

(21) Appl. No.: 18/985,251

(22) Filed: Dec. 18, 2024

(65) Prior Publication Data

US 2025/0208245 A1    Jun. 26, 2025

(30) Foreign Application Priority Data

Dec. 21, 2023   (DE) ...................... 10 2023 213 195.1

(51) Int. Cl.
*G01V 3/00* (2006.01)
*G01R 33/385* (2006.01)
(Continued)

(52) U.S. Cl.
CPC ....... *G01R 33/543* (2013.01); *G01R 33/3856* (2013.01); *G01R 33/4804* (2013.01); *G01R 33/56518* (2013.01)

(58) Field of Classification Search
CPC ............ G01R 33/3607; G01R 33/5608; G06T 11/005; G06T 11/006; G06T 2211/424
(Continued)

(56) References Cited

U.S. PATENT DOCUMENTS

2022/0091206 A1   3/2022   Eberler et al.

FOREIGN PATENT DOCUMENTS

DE   102020211844 A1 *  3/2022  ............. A61B 5/055

OTHER PUBLICATIONS

Bossavit, Alain; "On the numerical analysis of eddy-current problems"; Computer methods in applied mechanics and engineering, 1981, 27. Jg., Nr. 3, S. 303-318. DOI: https://doi.org/10.1016/0045-7825(81)90135-3.

(Continued)

*Primary Examiner* — Walter L Lindsay, Jr.
*Assistant Examiner* — Frederick Wenderoth
(74) *Attorney, Agent, or Firm* — Harness, Dickey & Pierce, P.L.C.

(57) ABSTRACT

A computer-implemented method for estimating an influence of a magnetic resonance tomography sequence on at least one component in or on an examination tunnel of a magnetic resonance tomography system, wherein the method comprises inputting at least one gradient waveform of the magnetic resonance tomography sequence into a temperature model; calculating an increase in temperature caused by an application of the magnetic resonance tomography sequence in the at least one component using the temperature model, the temperature model configured to calculate the increase in temperature based on an estimation of eddy currents induced by the at least one gradient waveform in the at least one component; and outputting at least one of the calculated increase in temperature or a temperature achieved by the increase in temperature.

13 Claims, 6 Drawing Sheets

(51) Int. Cl.
  *G01R 33/48* (2006.01)
  *G01R 33/54* (2006.01)
  *G01R 33/565* (2006.01)

(58) Field of Classification Search
  USPC .......................................................... 324/309
  See application file for complete search history.

(56) References Cited

OTHER PUBLICATIONS

German Office Action and English translation thereof for German Application No. 10 2023 213 195.1 mailed Nov. 12, 2024.
German Decision to Grant and English translation thereof for German Application No. 10 2023 213 195.1 mailed Dec. 17, 2024.

* cited by examiner

ESTIMATING AN INFLUENCE OF A MAGNETIC RESONANCE TOMOGRAPHY SEQUENCE ON AT LEAST ONE COMPONENT IN OR ON AN EXAMINATION TUNNEL AND PROTECTION OF THE COMPONENT

CROSS-REFERENCE TO RELATED APPLICATION(S)

The present application claims priority under 35 U.S.C. § 119 to German Patent Application No. 10 2023 213 195.1, filed Dec. 21, 2023, the entire contents of which is incorporated herein by reference.

FIELD

One or more example embodiments relates to a method for estimating an influence of a magnetic resonance tomography sequence on at least one component in or on an examination tunnel of a magnetic resonance tomography system, to a method for protection of at least one component in or on an examination tunnel of a magnetic resonance tomography system, to a corresponding computer program and to a magnetic resonance tomography system.

Independent of the grammatical term usage, individuals with male, female or other gender identities are included within the term.

RELATED ART

Through the large magnetic fields, in particular also the large changes in magnetic fields, which arise in an examination tunnel of magnetic resonance tomography systems (MRT systems), the danger exists of damaging components in the examination tunnel.

SUMMARY

A problem can arise in particular when a further imaging system is combined with the MRT system. For example it is usual to combine a Positron Emission Tomography system (PET system) with MRT systems. PET detector cassettes (DEAs) can be provided in such combined MR-PET systems for example for time-resolved spatial localization of the Gamma radiation in the examination tunnel of the MRT system. The influence of an MRT scan can cause high temperatures, for example temperatures of up to 400° C., to occur in the DEAs. Such temperatures are suitable for destroying the DEAs. But far lower temperatures that possibly may not directly destroy the DEAs can also lead to the functionality of the DEAs being adversely affected.

One or more example embodiments provides a possibility with which the safety of one or more components in and examination tunnel can be increased and/or with which the influence of an MRT scan on the components can be determined.

BRIEF DESCRIPTION OF THE DRAWINGS

Forms of embodiment are described below with reference to the enclosed figures.

DETAILED DESCRIPTION

Figure 1:
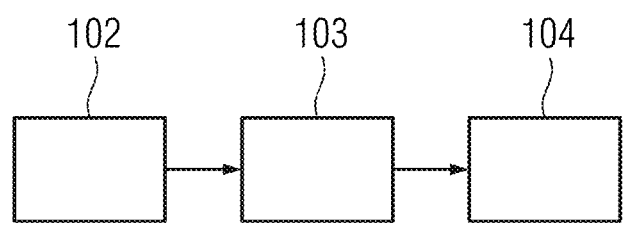
FIG. 1 shows a flow diagram of a computer-implemented method for estimating an influence of a magnetic resonance tomography sequence on at least one component in or on an examination tunnel of a magnetic resonance tomography system in accordance with one embodiment of the invention.
Figure 2:
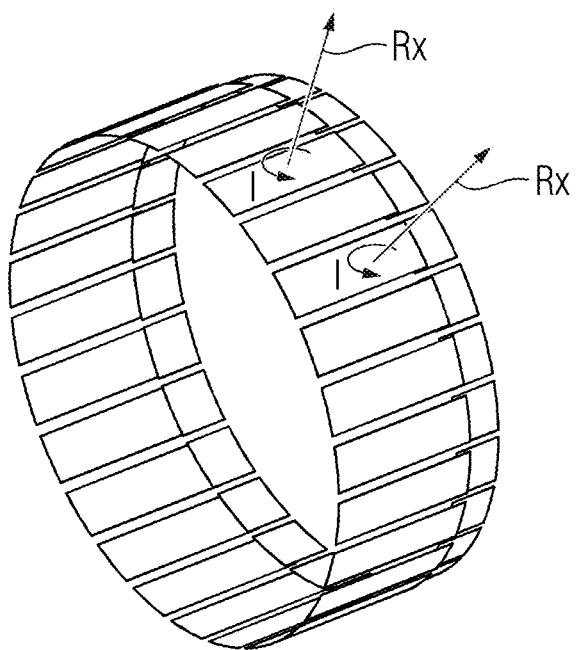
FIG. 2 shows a number of components of an inventive system and the alignment of two example radial vectors.

In accordance one or more example embodiments a computer-implemented method for estimating an influence of a magnetic resonance tomography sequence on at least one component in or on an examination tunnel of a magnetic resonance tomography system, in particular of a combined Magnetic Resonance Tomography/Positron Emission Tomography system, is provided. The method comprises the following steps:

(a) Entering at least one gradient waveform of the magnetic resonance tomography sequence into a temperature model;

(b) With the temperature model: Calculating an increase in temperature in the at least one component caused by an application of the magnetic resonance tomography sequence, wherein the temperature model is designed so that it carries out the calculation of the increase in temperature on the basis of an estimation of eddy currents induced by the at least one gradient waveform in the at least one component;

(c) Outputting the calculated increase in temperature and/or a temperature reached by the increase in temperature from the temperature model.

The magnetic resonance tomography system (MRT system) can be a combined system, in that a magnetic resonance tomograph is combined with a further imaging modality. For example the magnetic resonance tomography system can be a combined Magnetic Resonance Tomography/Positron Emission Tomography system (MR-PET system). The examination tunnel can in particular be an MR tube. The examination tunnel can also be referred to as the MR bore. The at least one component can preferably be a component that can be heated up by the influence of magnetic fields. A heating up by the influence of magnetic fields can in particular occur through magnetically induced eddy currents. The at least one component is preferably a component that can be heated up due to eddy currents. The at least one component can in particular comprise electrically conductive portions. For example the at least one component can be or can comprise a component of the further imaging modality. Other components in the examination tunnel can however be monitored in accordance with one or more example embodiments. The at least one component can comprise a part of the MRT system itself. For example the at least one component can comprise a part of a movement monitoring system, a part of a communication and/or information system (for a patient in the examination tunnel for example) and/or a body coil of the MRT. In MR-PET systems PET detector cassettes (DEAs) are usually located inside the examination tunnel. The at least one component can be or can comprise a component of the PET. The at least one component can in particular comprise at least one PET detector cassette. The PET detector cassettes can be intended for a temporally resolved spatial location of Gamma radiation. The PET detector cassettes can be arranged in the shape of a ring in the examination tunnel. The orientation of the ring-shaped arrangement of the PET detector cassettes can correspond to a ring-shaped cross section of the examination tunnel. The PET detector cassettes are preferably arranged between a whole body coil and a gradient coil of the MRT system. While the inventive method can be used in general for various components, the method can be especially advantageous for protection of the PET detector cassettes. The PET detector cassettes can be damaged or even destroyed by temperatures that are too high. This can adversely affect the functionality of the PET detector cassettes or completely nullify it.

Depending on the magnetic resonance tomography sequence (MRT sequence) applied, the result can be a flow of current, which is based on induced eddy currents, through the at least one component. The eddy currents can be based in particular on a change in the gradient signals of the individual gradient coils of the MRT system. A change in the gradient signals typically corresponds to the slew rate of the gradient signals. The eddy currents can lead to an increase in the temperature of the at least one component. The influence of the MRT sequence thus in particular comprises an influence on the temperature of the at least one component. Large-surface conductive components or portions of components, for example large-surface copper mass planes of DEA electronics boards, can be especially susceptible to such heating up. The increase in temperature can stem in such cases in particular from an overlaying of various gradient fields of various gradient coils (in particular of the x, y and z coil). Basically it is conceivable for example, in order to reduce the danger for the at least one component, to test scan protocols with magnetic resonance tomography sequences beforehand. Thus a combined MRT system could have preset protocols with which a start could be made with sufficient safety for the at least one component. It has been recognized however that a deviation from such preset protocols can occur. Through this new combinations of gradient fields can result, which can possibly lead to an increased heating up. For example a slice in accordance with a preset protocol can be flipped in a change of the protocol, whereby the proportion of the various gradients can be changed and thus possibly also the resulting overall influence on the at least one component. Advantageously with the inventive method an increase in temperature that might possibly occur can already be recognized in advance of a measurement, even when a previously unknown MRT sequence is to be tried out. Advantageously, with the inventive method, development of an MRT system can be simplified, in that it can already be established beforehand whether relevant MRT sequences could cause a critical increase in temperature. For example "virtual engineering" can be made possible, in that hardware components can already be optimized beforehand based on the intended MRT sequences. For example the question of whether clinically relevant special sequences or only technical special sequences can lead to an increased temperature is also able to be clarified at an early stage. Technical special sequences can be special sequences that are not needed for normal clinical use, but which are still basically able to be carried out. While it is usually assumed in development that such special sequences are not used, there can still be their (unforeseen) use, for test purposes for example.

Advantageously it can also be determined with the inventive method in these cases at an early stage, i.e. in particular even before the actual beginning of the special sequence, whether an increase in temperature in the at least one component is to be expected. The information obtained by the method can be used for example in order to warn a user, to propose a change of MRT sequence to the user or to carry it out automatically, and/or automatically to prevent the MRT sequence being carried out for a recognized increase in temperature to be expected.

The term "gradient waveform" is to be understood in broad terms. It relates in general to the waveform of at least one gradient coil provided for in accordance with the MRT sequence. For example the gradient waveform can be the magnetic field which is produced in gradient coils by am MRT sequence provided for in the activation of the gradient coil, (for example locally or as a spatial distribution). It is also conceivable for the gradient waveform to be entered as the supply of power to at least one gradient coil, from which the gradient field can be derived. The gradient waveform can optionally also be described by the change in the gradient field, for example by specification of the (time-dependent) slew rate of the respective gradient coil or of the respective gradient. The gradient waveform can be defined by a gradient pulse. For example the gradient waveform can comprise a periodically recurring gradient pulse.

Within the framework of the inventive method the gradient waveform is entered into a temperature model. The temperature model can be a physical model. The temperature model can for example comprise a computer algorithm. The temperature model is in particular embodied for carrying out the calculation of an increase in temperature in the at least one component on the basis of an estimation of eddy currents induced by the at least one gradient waveform in the at least one component. In accordance with one or more example embodiments an increase in temperature caused by an application of the magnetic resonance tomography sequence is calculated with the temperature model. The calculation can in this case comprise an approximate estimation. Advantageously a local heating up can also be able to be established by a calculation via induced eddy currents. It can be taken into account that eddy currents with different strengths occur at various points of the at least one component. The heating up of the component can also turn out differently locally through this. For example the components as a whole can only heat up slightly, but locally markedly more however. Through this local heat-related damage can in principle occur.

Finally the calculated increase in temperature is output. This is generally to be understood in broad terms. The increase in temperature can be output in the form of an absolute temperature, which can be understood in relation to a reference temperature. The absolute temperature can be the temperature achieved. The "temperature achieved" in this case is in particular to be understood in such a way that it is the temperature of the at least one component that reaches said temperature through the increase in temperature or is expected to do so. The reference temperature can for example be the temperature of the at least one component in an idle state of the MRT system. The reference temperature can be a room temperature for example. The increase in temperature can be output by the temperature model to a further entity for example. The further entity can be a monitoring algorithm for example. The monitoring algorithm can be embodied to compare the increase in temperature with a maximum permitted increase in temperature or a calculated temperature with a maximum permitted temperature. The monitoring algorithm can be embodied to initiate a measure if the maximum permitted temperature or increase in temperature is exceeded. The measure can for example be the output of an alarm, of user information or of a control signal. The user information can for example relate to the predicted temperature of the at least one component that will be too high and/or to a proposal for a change of the MRT sequence. The control signal can for example comprise prevention of the execution of the MRT sequence and/or a change to the MRT sequence.

In accordance with one embodiment the temperature model, for calculation of the increase in temperature, takes account both of at least one amount of heat taken up and at least one amount of heat given out of the at least one component. The at least one amount of heat taken up can in particular comprise heat induced by the eddy currents. The at least one amount of heat given out can for example be an aspect of the heat emission that is responsible for the greatest emission of heat. The at least one amount of heat given out can for example comprise heat given out via thermal conductivity and/or heat given out via thermal radiation. Advantageously, with this embodiment, there can be a balance between heat given out and heat taken up. In particular, in that not only the heat taken up, but also a heat loss in the form of the heat given out is taken into account, a more precise estimation of the temperature development or increase in temperature can be achieved. For example the energy balance can be defined via an equation in the form $$\Delta Q = \Delta Q^+ + \Delta Q^- \quad (1)$$

wherein $\Delta Q^+$ is heat taken up and $\Delta Q^-$ is heat given out. The heat taken up and/or the heat given out can be time-dependent.

If it is assumed for example that the heating up $\Delta Q^+$ depends on an induced power P(t), which in its turn is dependent on a change in the gradient field $\dot{G}$, which can be defined by a slew rate S of the gradients, then the amount of heat taken up can be $$\Delta Q^+ = P(t)\Delta t \sim S^2(t)\Delta t = \dot{G}^2(t)\Delta t \quad (2)$$

The heat taken up $\Delta Q^+$ can be calculated for example for a reference pulse of the magnetic resonance tomography sequence. The reference pulse can for example be a sawtooth pulse. The heat taken up $\Delta Q^+$ can for example be calculated for a number of positions in the at least one component. The heat taken up $\Delta Q^+$ can be calculated separately for each gradient axis (for example for each of the three gradient axes x, y, z). G or $\dot{G}$ can be a gradient vector. The gradient vector can for example be a general 3D vector. According to the heat input a gradient vector can be calculated for example for a number of positions in the at least one component. The gradient vector can be calculated separately for each gradient axis (for example for each of the three gradient axes x, y, z). For a sequence with overlaid gradient pulses a vector sum can be formed for example. Based on the overlaid gradient pulses a resulting total input of heat (for example $Q_x^+ + Q_y^+ + Q_{zx}^+$) can be calculated.

If it is assumed that the heat given out $\Delta Q^-$ by a heat emission is determined by an emission coefficient x, the heat given out can be defined for example by $$\Delta Q^- = \chi(T-T_0)\Delta t \quad (3)$$

wherein T is the temperature and $T_0$ is the ambient temperature, wherein $$T = \frac{Q}{c}$$

with the thermal capacitance c applies.

In accordance with one embodiment the temperature model carries out the calculation of the increase in temperature based on the solution of a differential equation, wherein the differential equation relates to changing the temperature of the at least one component and comprises at least an amount of heat, preferably at least two amounts of heat. The differential equation can be based on an energy balance equation. For example, starting from the above-mentioned energy balance (equation 1), the differential equation can have the form $$\dot{T}(t) = k_1 \frac{\Delta Q^+}{\Delta t} - k_2 \frac{\Delta Q^-}{\Delta t} \quad (4)$$

wherein $\dot{T}(t)$ is the change of temperature over the time t and $k_1$ and $k_2$ are constants. With equation 2 and equation 3 and also with a temperature decay constant $\tau = c/\chi$, the differential equation (equation 4) can assume the concrete form $$\dot{T}(t) = \frac{1}{c}\dot{G}^2(t) - \frac{1}{\tau}(T(t) - T_0) \quad (5)$$

The solution of this differential equation 5 enables a development of heat in the at least one component to be estimated. The differential equation can for example be solved numerically. The differential equation can for example be solved by an algorithm that is embodied for solving differential equations, in particular for numeric solution of differential equations. The algorithm can be part of the temperature model.

In accordance with one embodiment the temperature model, to calculate the change in temperature, calculates at least one radial vector that is characteristic of an induced eddy current and is perpendicular to a surface of the at least one component. The radial vector can in particular characterize a change of the magnetic flux perpendicular to the surface. In particular the radial vector can specify a measure for the change in the magnetic flux at the location of the at least one component. If it is assumed that the at least one component is arranged or installed at a fixed intended location, then it can be assumed for example that a distance between a specific gradient coil and the at least one component and/or a (geometrical) arrangement of the at least one component relative to the gradient coil is always the same. Accordingly for example it can be assumed that a relative gradient field at the location of the at least one component is always the same. The radial vector can be characteristic for the relative gradient field. The radial vector can have a value that is characteristic for the relative gradient field. The value can in particular correspond to an amount of the radial vector, wherein the value can preferably have a leading sign. In other words the value can be both negative and also positive. The leading sign of the value can correspond to the direction of the gradient field change in parallel to the radial vector. Thus, according to the orientation of the field change, the radial vector can point in one of two opposite directions.

Advantageously the value of the radial vector can be determined once. For example the value of the radial vector can have been determined beforehand on the basis of the geometry of one or more gradient coils for the at least one component. With a number of components a value of a radial vector can have been determined beforehand as a result of the geometry of one or more gradient coils for each component. For example the value of the radial vector or the values of the radial vectors can have been determined by a simulation. The values for various components can be stored as a table for example. There can be provision for the value of the radial vector to be representative of the entire at least one component. For example the value can be a value summed over the entire range of the at least one component relevant for the eddy current induction. The relevant range can in particular comprise contiguous conductive mass surfaces (in which in particular eddy currents can be induced that are classified as critical). The classification can for example can be carried out by individual estimation of an expert and/or by simulation/measurement and a threshold value. The threshold value can for example be a temperature threshold value or an induction current threshold value. The value can be determined for example by simulation, calculation or measurement. For example the value can be calculated back from an exemplary measurement or simulation of a temperature determination. A relative gradient field is to be understood in this context relative to another location, for example relative to a location of a further component. An absolute gradient field or a change to the absolute gradient field at the location of the at least one component can for example still depend on the respective MRT sequence, i.e. in particular on the respective change in the gradient field in accordance with the MRT sequence. An absolute gradient field can in this context be the actual gradient field, including the geometry and the MRT sequence (i.e. the current for example which is conducted through the gradient coil in order to create the gradient field). For example the gradient field, at a first location on the at least one component, can have a relative size of 0.5 and at a further location (for example the location of a further component) can have another relative size of 2.8. Accordingly for example the radial vector at the location of the at least one component, can have the value 0.5 and the value of another radial vector at a further location of a further component can amount to 2.8. Depending on the respective MRT sequence, a value can be established in this example (for example by multiplication of the value 0.5 by a factor that depends on the MRT sequence), which is representative for the actual value of the field change at the location of the at least one component. The change in the magnetic flux is typically proportional to the induction voltage, which brings about a current or an eddy current in the components, and to the change of the magnetic field. The radial vector can correspond to the changing gradient field and/or be in a fixed ratio to the gradient field. For example the radial vector can be proportional to the changing gradient field. The heat transmission or amount of heat can be derived from the radial vector. It can be assumed for example that an induced voltage and/or a changing gradient field is proportional to the root of the heat transmission. A number of radial vectors can be provided in each case for one of a number of components and/or in each case for one of a number of positions on a component. A radial vector can describe a relative amount of a gradient field created by one of the gradients for an eddy current induced in a component. Preferably the radial vector can be perpendicular to a surface of the at least one component or to a plane of the at least one component, in which an eddy current is induced. The surface can in particular be the largest surface of the at least one component. For example the surface can be a mass plane of a circuit board, in particular an electronics circuit board. The mass plane can for example be a copper mass plane. The board can be for example be an electronics circuit board of a PET detector cassette or a DEA electronics circuit board. The radial vector can be an efficient and reliable option for predicting a development of heat based on eddy currents. For example, in the determination of a development of heat, spatial directions that are not perpendicular to the surface of the components and therefore do not induce any significant eddy currents can be ignored.

In accordance with one embodiment the magnetic resonance tomography sequence comprises a number of gradient coils, in particular at least two or three gradient coils, or the activation of a number of gradient coils each with at least one gradient waveform, wherein at least one radial vector is provided for each of the gradient coils. With a number of components, for each of the number of components, at least one radial vector is provided for each of the gradient coils. In particular each radial vector can specify a measure for the change in the magnetic flux at the location of the at least one component caused by the respective gradient coil. Each of the radial vectors can be characteristic for the relative gradient field of the corresponding gradient coil in each case. Each radial vector can have a value that is characteristic for the respective relative gradient field. Advantageously the value of the radial vectors can have been determined once. For example the value of the radial vectors can have been determined as a result of the geometry of the gradient coils for the at least one component, in particular by simulation. With a number of components, a value of a radial vector can be determined for each component in each case for each gradient coil as a result of the geometry of the gradient coils. The values for various components and/or various gradients can be stored as a table for example. The values of the table can have been determined by simulation for example. The table with the values can be structured as follows for example (Table I):

TABLE I

| Components # | Value for x gradient $U_x$ | Value for y gradient $U_y$ | Value for z gradient $U_z$ |
|---|---|---|---|
| 1 | 0.5 | 5.0 | −0.6 |
| 2 | −0.3 | −4.5 | 0.5 |
| 3 | −2.1 | −5.0 | 0.5 |
| etc. | etc. | etc. | etc. |

The values of the radial vector can be converted into the heat entry using a factor that is established by a calibration and/or by using at least one adaptation dependent on the MRT sequence (for example a further factor). For example the gradient field, through an x gradient, can have a relative size of 0.5 at the location of the at least one component and the gradient field, through a y gradient, a relative size of 5.0 at the location of the at least one component and the gradient field, through a z gradient, a relative size of −0.6 at the location of the at least one component. The overall flux can then be determined for example by overlaying the fields caused by the various gradient fields. Because the radial vectors are all perpendicular to the surface, they are aligned in parallel with one another. Therefore the determination of the overlay is relatively simple and can be established for example by simple addition. Through the use of radial vectors perpendicular to the surface of the components, instead of a vector addition, advantageously a simple addition of the vector amounts can be used. Depending on the respective MRT sequence, a value can be established that is representative for the actual value of the field change at the location of the at least one component. For example the change in magnetic flux or the change in the gradient field can be determined from the value of each radial vector for each gradient field together with at least one characteristic value for the waveform of the respective gradient field in accordance with the MRT sequence. In the example given, the value of the first radial vector (for example 0.5) can be multiplied by a characteristic value of the x gradient, the value of the second radial vector (for example 5.0) by a characteristic value of the y gradient, and the value of the third radial vector (for example −0.6) by a characteristic value of the z gradient. This embodiment can be especially advantageous when the at least one component is located especially close to the gradient coils. For example PET detector cassettes are typically very close to the gradient coils. If the at least one component is located especially close to the gradient coils, then the near field development of the gradient field can be relatively inhomogeneous. For example it has been determined that the near field development at PET detector cassettes can be very inhomogeneous for X and Y saddle coils, in particular below the centers of the windings of the coils. The winding centers can also be referred to as eyes of the coils. With such proximity of the at least one component to the gradient coils the gradient fields on the at least one component are not aligned perpendicular to one another and can moreover be unevenly distributed. For example the gradient fields can be distributed unevenly over the positions of PET detector cassettes arranged in the shape of a ring. The formation of a vector sum can be numerically unstable, which can render the calculation or prediction of the temperature development more difficult. Here this embodiment with radial vectors can be especially advantageous. Based on the radial vectors a heat input or the heat taken up at the at least one component can be determined as an induction current with a leading sign, which, depending on the respective gradient, is perpendicular to a surface of the components (for example perpendicular to a DEA circuit board). In this case the radial vectors of all gradient points can advantageously point in the same perpendicular direction (namely in the direction of the radial vector). Thus a simple vector summation can be used in order to calculate a sum of the heat input. The representation as perpendicular to the surface is advantageous, especially with flat components, such as for example circuit boards or electronics circuit boards. With flat components it can typically be assumed that, in any event, only a radial portion perpendicular to the flat surface contributes significantly to the heating up by induction.

In accordance with one embodiment the amount of heat produced by the induced eddy currents is calculated in that the contributions of the gradient fields to an induction voltage are weighted with a respective slew rate of the gradient coils. With just one radial vector, the contribution of the gradient field to the induction voltage can accordingly be weighted with the slew rate of the gradient coil. The slew rate can be the slew rate provided in accordance with the MRT sequence. Advantageously a change in a magnetic flux or in the gradient field can be proportional to the value of the radial vector and the slew rate. The absolute change in the gradient field $\dot{G}$ can be determined by multiplication of the value of the radial vectors by the slew rate. In accordance with equation 2 the heat input $\Delta Q^+$ can be proportional to the change in the squared gradient field $\dot{G}^2(t)$ or the squared induced voltage. The contributions of a number of gradient coils or gradient fields can be determined by weighted addition of the values of the radial vectors with the respective slew rate of the gradient coils. For example the values of three radial vectors ($U_x$, $U_y$, $U_z$) each with a slew rate ($S_x$, $S_y$, $S_z$) of three gradient coils (x, y, z) can be used by addition to determine the heat input ($\Delta Q^+$) over a specific period of time ($t_{sample}$):

$$\Delta Q^+ \sim (s_x \times U_x + S_y \times U_y + s_z \times U_z)^2 \times t_{sample} \quad (6)$$

wherein in particular $\dot{G}^2(t_{sample})$ can be proportional to or equal to $(s_x \times U_x + S_y \times U_y + s_z \times U_z)^2 \times t_{sample}$. Correspondingly the values of the radial vectors can have been determined once (based for example, as a result of the geometry of the gradient coils, on the position of the at least one component and/or on a simulation) and be able to be used for a given field change (which is included through the slew rates $s_x$, $s_y$, $s_z$ in the calculation). The respective slew rate can be dependent on the MRT sequence applied. The values of the slew rate ($s_x$, $s_y$, $s_z$) do not necessarily have to be the actual slew rate, but they can for example also correspond to the slew rate. The values of the radial vectors ($U_x$, $U_y$, $U_z$) can correspond to a reference pulse, wherein the values can be further calculated based on the slew rate. In particular the slew rates used in the determination of the values used in the weighting as reference variables can be taken into account. Accordingly the values of the slew rate can be a conversion factor from the reference pulse to the actual pulse. Depending on the respective MRT sequence, some values of the slew rate for example can also be zero. It is also conceivable for the calculated sum (depending on the slew rates) with partly positive and partly negative values of the radial vectors to become zero. This corresponds to a destructive overlaying of the magnetic fields at the location of the at least one component. With a number of components for example, the heat input for at least one component can be zero, but not for one or more further components. The slew rates can be time-dependent. At least one calibration factor can be provided, in particular in addition to the weighting with the slew rates. The calibration factor can have been determined by a calibration measurement. For example the calibration factor can be a thermal capacitance constant or can depend on a thermal capacitance constant.

In accordance with one embodiment the temperature model is tailored to the at least one component, in particular by at least one calibration measurement. For example the temperature model can comprise information about at least one property of the at least one component. The at least one property can in particular relate to a temperature behavior of the at least one component. For example the at least one property can relate to the capability of the at least one component to take up and/or give out heat. The at least one property can be a material-dependent and/or a geometry-dependent property. Advantageously the temperature model can thus take account of one or more peculiarities of the at least one component and can achieve a greater accuracy.

In accordance with one embodiment the temperature model comprises at least one characteristic physical constant relating to the temperature waveform of the at least one component. The characteristic physical constant can in particular be one or more of the following: A thermal capacitance constant of the at least one component, a thermal time constant of the at least one component, a delay in the occurrence of the induced eddy currents relative to the gradient waveform set. The physical constant can have been determined by a calibration measurement. The thermal time constant can be a cooling time constant. The cooling time constant can be characteristic for how fast the at least one component cools down or at what rate it gives out heat. The thermal time constant can for example depend, through a heat radiation behavior of the at least one component or through a heat dissipation, on the at least one component. The heat dissipation can in particular also depend on the environment or on the installation of the at least one component.

The thermal time constant can be determined by a calibration measurement. For example in a calibration measurement an MRT sequence can be activated and subsequently switched off. After the MRT sequence is switched off the temperature waveform of the components can be further logged and fitted to an e-function. An e-function is a typical waveform of the temperature of a component after the MRT sequence has been switched off. The decay constant of the e-function can correspond to the thermal time constant. Advantageously a thermal time constant can thus in particular be able to be determined that is independent of the respective MRT sequence per se, i.e. that can be used for a number of MRT sequences.

A thermal capacitance constant is to be understood in broad terms within the framework of this invention. The thermal capacitance constant can be a thermal capacitance or be a variable linked to the thermal capacitance. For example the thermal capacitance constant can be a thermal capacitance, a specific thermal capacitance or a molar thermal capacitance. The thermal capacitance can link an amount of heat taken up to an increase in temperature of the component.

The thermal capacitance constant can be determined by a calibration measurement. For example an MRT sequence can be carried out until a thermal equilibrium is set as well as being simulated with the temperature model. The temperature of the at least one component can for example be measured with a temperature sensor. A calibration can be undertaken by the temperature of the thermal equilibrium of the simulation with the temperature model being adapted to the temperature of the measurement. Optionally the thermal capacitance constant can be determined by an initial increase in the temperature of the component on application of an MRT sequence. For the initial increase, with the mass m of the component, the power P and the time t over which this power acts (cf. equation 2) the following can apply:

$$dT=(P \times t)/(c \times m) \quad (7)$$

Whereby the specific thermal capacitance c $$c=(P \times t)/(dT \times m) \quad (8)$$

or the thermal capacitance $C = c \times m$ $$C = c \times m = (P \times t)/dT \quad (9)$$

can be determined.

Preferably the thermal time constant can also be used for determining the thermal capacitance constant, in particular in order to calculate the thermal equilibrium correctly. For example a combined calibration of thermal time constant and thermal capacitance constant can be provided. In the combined calibration for example an MRT sequence can be carried out until a thermal equilibrium is set (i.e. for example until the temperature of the component no longer changes significantly) and be simulated with the temperature model and the temperature waveform over time be recorded in each case. Subsequently the thermal time constant and then the thermal capacitance constant can be determined.

Through the inductivity of the at least one component an induced eddy current and thus also a delayed heating up can be set. In a few cases this delay can be negligible. In some cases however it can be important to determine the temperature waveform (in particular influenced by heating up and cooling down) as exactly as possible. This can be the case for example when an MRT sequence leads to an increase in temperature, which brings the at least one component very close to a possibly critical temperature. In this case or in other cases it can be very useful to determine as exactly as possible when an amount of heat is taken up. Correspondingly a delay in the occurrence of an induced eddy current relative to the gradient waveform can be calibrated. The delay can for example be determined by a comparison of measurement and simulation with the temperature model.

One or more example embodiments is a computer-implemented method for protection of at least one component in or on an examination tunnel of a magnetic resonance tomography system. The magnetic resonance tomography system can be a magnetic resonance tomography system combined with another imaging modality. The magnetic resonance tomography system can in particular be a combined Magnetic Resonance Tomography/Positron Emission Tomography system. The method comprises the following steps:

receipt of a magnetic resonance tomography sequence to be carried out with the magnetic resonance tomography system;

application of the method for estimating an influence of a magnetic resonance tomography sequence on at least one component in or on an examination tunnel of a magnetic resonance tomography system, as described herein;

checking whether the calculated increase in temperature is exceeding a predetermined temperature threshold;

if the temperature threshold is exceeded: Automatic adaptation of the magnetic resonance tomography sequence and/or output of proposal for adaptation of the magnetic resonance tomography sequence to a user.

All advantages and features of the method for estimating an influence of a magnetic resonance tomography sequence on at least one component in or on an examination tunnel can be transferred by analogy to the method for protecting at least one component in or on an examination tunnel and vice versa. Advantageously with this aspect a protection against damage to the at least one component can be achieved, in that even before the magnetic resonance tomography sequence (MRT sequence) is carried out, it can be established whether too high a temperature of the component is possibly being reached. This can also be advantageous in relation to monitoring the temperature during the measurement (by temperature sensors for example), because with this the method can be prevented from even being started. Thus for example a risky temperature development can be avoided in advance. Moreover an unnecessary starting of a sequence, which would then have to be aborted, can be prevented, by which time and possibly costs can be saved for example. This method can also be advantageous for possibly avoiding examinations on a patient that are stress-inducing or dangerous to health (for example with the use of radioactive PET contrast media), which would then have to be aborted.

In particular, even with the application of newly developed MRT sequences, this method can be advantageous, because it can be established even before testing whether the respective MRT sequence can be carried out, without it resulting in questionably high temperatures of the at least one component. For example modifications of the MRT sequence can be proposed to a user. A modification can for example be a restriction of the slew rate, a VERSE pulse, an increase in the TR, a change in the gradient setting from "high" to "normal" or "whisper" and/or a parameter restriction etc.

One or more example embodiments is a computer program comprising a temperature model, as described herein. The computer program can in particular comprise commands that, when the program is executed by a computer, cause said computer to carry out the steps of a method as described herein. All advantages and features of the method for estimating an influence of a magnetic resonance tomography sequence on at least one component in or on an examination tunnel and of the method for protection of at least one component in or on an examination tunnel can be transferred by analogy to the computer program and vice versa. The computer program can for example be stored on a computer-readable memory medium, in particular a non-volatile memory medium. The memory medium can for example be a hard disk, an SSD, a flash memory, an online server, etc.

One or more example embodiments is a method for calibrating a temperature model, in particular a temperature model as described here. The method for calibrating a temperature model comprises the following steps:
- calculation of a temperature waveform of a component that is arranged in an examination tunnel of a magnetic resonance tomography systems, during and after the application of a magnetic resonance tomography sequence with the temperature model;
- carrying out the magnetic resonance tomography sequence and measurement by sensors of the temperature waveform during and after the carrying out of the magnetic resonance tomography sequence;
- comparison of the calculated and measured temperature waveform in order to determine a thermal time constant and/or a thermal capacitance constant of the component;
- adaptation of the temperature model with the thermal time constant determined and the thermal capacitance determined.

The thermal time constant can be determined for example by comparison of a calculated and measured drop in temperature after the end of the magnetic resonance tomography sequence. The thermal capacitance constant can be determined for example by comparison of a calculated and measured thermal equilibrium and/or a calculated and measured initial increase in the temperature during the magnetic resonance tomography sequence. All advantages and features of the method for estimating an influence of a magnetic resonance tomography sequence on at least one component in or on an examination tunnel and of the method for protection of at least one component in or on an examination tunnel can be transferred by analogy to the method for calibration of a temperature model and vice versa. In particular the advantages, steps and features for calibration, which are explained within the framework of the other methods can also be applied to the method for calibration.

One or more example embodiments is a magnetic resonance tomography system with a control module, which comprise a computer program as described herein. The magnetic resonance tomography system can in particular be embodied to carry out a method as described herein. All advantages and features of the method for estimating an influence of a magnetic resonance tomography sequence on at least one component in or on an examination tunnel, of the method for protection of at least one component in or on an examination tunnel, of the computer program and of the method for calibrating a temperature model can be transferred by analogy to the magnetic resonance tomography system and vice versa.

All forms of embodiment described herein can be combined with one another, provided something different has not been specified explicitly.

FIG. 1 shows a flow diagram of a computer-implemented method for estimating an influence of a magnetic resonance tomography sequence on at least one component in or on an examination tunnel of a magnetic resonance tomography system, in accordance with one embodiment of the invention. The magnetic resonance tomography system can in particular be a combined Magnetic Resonance Tomography/Positron Emission Tomography system.

In a first step 102 at least one gradient waveform of the magnetic resonance tomography sequence is entered into a temperature model. Preferably the temperature model is tailored to the at least one component. For example the temperature model can comprise at least one characteristic physical constant relating to the temperature waveform of the at least one component. The at least one characteristic physical constant can for example be a thermal capacitance constant of the at least one component and/or a thermal time constant of the at least one component and/or a delay in the occurrence of an induced eddy current relative to the gradient waveform. For example the temperature model can be tailored by one or more calibration measurements to the at least one component.

In a further step 103 an increase in temperature in the at least one component, which is caused by the application of the magnetic resonance tomography sequence, can be calculated with the temperature model. In this case the temperature model is embodied so that it carries out the calculation of the increase in temperature on the basis of an estimation of eddy currents induced by the at least one gradient waveform in the at least one component. For calculation of the increase in temperature at least one amount of heat taken up by the at least one component is used. The amount of heat taken up can in particular be a heat induced by the eddy currents. Preferably at least one amount of heat given of the at least one component is taken into account for the calculation. Heat can be given out by thermal conductivity and/or thermal radiation for example. For example the temperature model can carry out the calculation of the increase in temperature based on the solution of a differential equation, which relates to the change in the temperature of the at least one component and takes account of one or more amounts of heat. For example a differential equation in accordance with equation 5 can be used, wherein the differential equation relates to the change in temperature of the at least one component and comprises at least one amount of heat, preferably at least two amounts of heat. Preferably just the portions of gradient fields that are perpendicular to a surface of the components can be used to do this. These can be characterized by a radial vector R, which is perpendicular to a surface of the respective component and which characterizes the relative amount of the gradient field at the respective point or component in the direction of the radial vector Rx. The current I induced by the respective gradient field is then proportional to the radial vector Rx and the respective slew rate. Figure shows 2 a schematic of a number of components, for example an arrangement of DEA electronics boards of a PET system, and the alignment of two example radial vectors via which in each case an induced current and thus also induced heat can be determined. The ratio of a number of gradient coils to the induced current can be determined in that the relative contributions or values (for example $U_x$, $U_y$, $U_z$) of the gradient coils, represented by a radial vector Rx, y, z in each case (which is perpendicular to the surface and can be positive or negative), weighted with the slew rate of the respective gradient coils, are added up (see for example equation 6).

In a further step 104 the calculated increase in temperature and/or a temperature reached by the increase in temperature is output from the temperature model.

Figure 3:
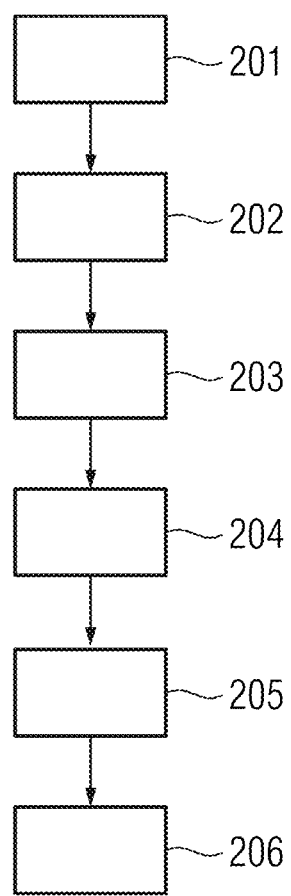
FIG. 3 shows a flow diagram of a computer-implemented method for protection of at least one component in or on an examination tunnel of a magnetic resonance tomography systems in accordance with one embodiment of the invention.

FIG. 3 shows a flow diagram of a computer-implemented method for protection of at least one component in or on an examination tunnel of a magnetic resonance tomography system in accordance with an embodiment of the invention. The magnetic resonance tomography system can in particular be a combined Magnetic Resonance Tomography/Positron Emission Tomography system. In a first step 201 a magnetic resonance tomography sequence, which is intended to be carried out with the magnetic resonance tomography system, is received. The next steps 202-204 can correspond to the steps 102-104 of the method that is described in FIG. 1. In a further step 205 a check is made as to whether the calculated increase in temperature is exceeding a predetermined temperature threshold. This can for example be undertaken by a simple threshold value reconciliation. Optionally various threshold values can be provided for various components and/or for various points on one or more components. In a further step 206, if the temperature threshold is exceeded, the magnetic resonance tomography sequence is adapted automatically. As an alternative or in addition, in this step 206 a proposal for adapting the magnetic resonance tomography sequence can be output to a user. In particular an adaptation can be proposed that does not lead to the temperature threshold being exceeded, for example by at least one parameter of the sequence (for example a duration) being adapted.

Figure 4:
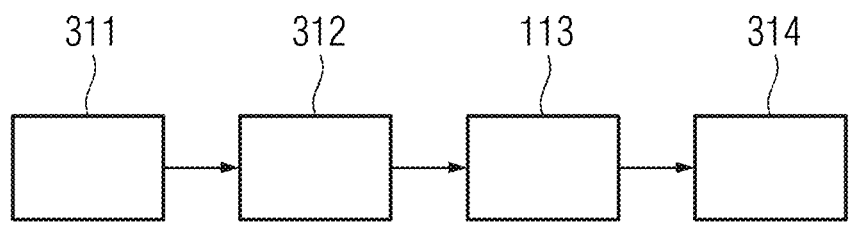
FIG. 4 shows a flow diagram of a method for calibration of a temperature model in accordance with one embodiment of the invention.
Figure 5:
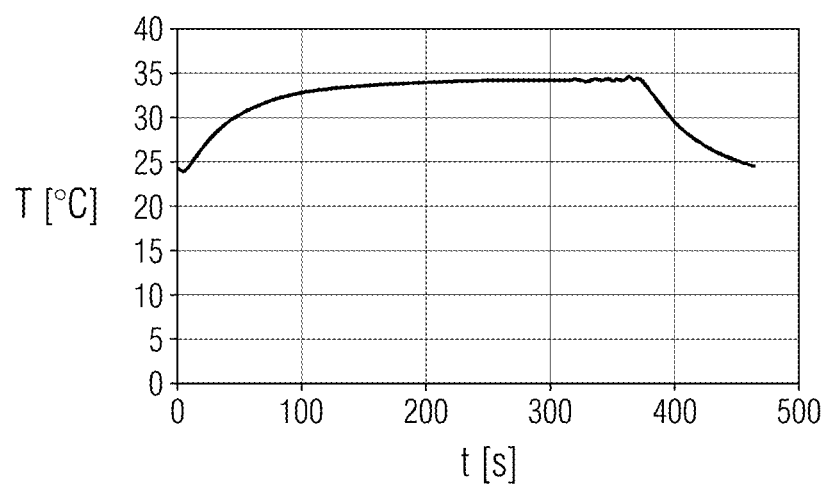
FIG. 5 shows a temperature waveform that would be calculated with a temperature model in accordance with one embodiment of the invention.
Figure 6:
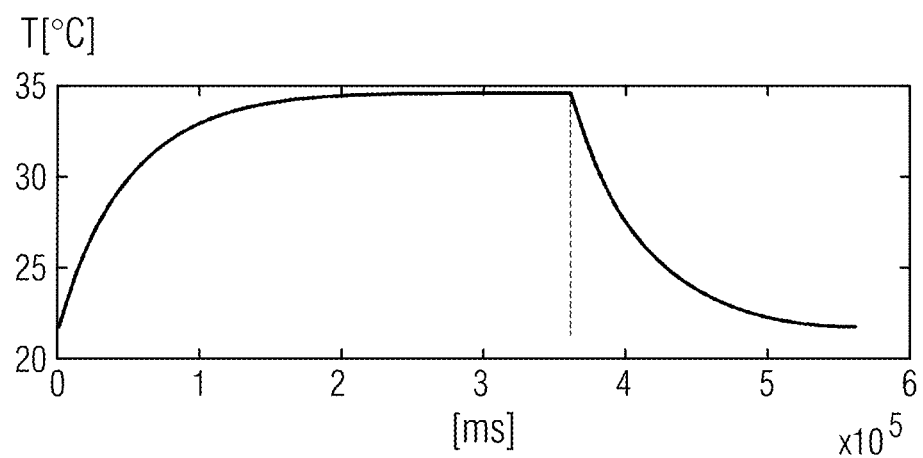
FIG. 6 shows a temperature waveform of a measurement, which corresponds to the calculated temperature waveform shown in FIG. 5.

FIG. 4 shows a method for calibration of a temperature model. The temperature model can in particular be a temperature model that (after the calibration) is applied in a method, as described in FIG. 1 or in FIG. 3. In a first step 311 of the method a temperature waveform of a component that is arranged in an examination tunnel of a magnetic resonance tomography system is calculated. The temperature waveform is calculated during and after the application of a magnetic resonance tomography sequence with the temperature model. FIG. 5 shows such a temperature waveform, which has been calculated with a temperature model. In a further step 312 the magnetic resonance tomography sequence is carried out, and the actual temperature waveform is measured by sensors, for example with temperature probes, during and after the magnetic resonance tomography sequence has been carried out. The temperature waveform of a corresponding measurement is shown in FIG. 6. In the two FIGS. 5 and 6 the point in time at which the MR sequence is switched off can clearly be seen at the occurrence of the drop in temperature. The point in time of the switch off is moreover marked by a dashed line in FIG. 6. In a further step 313, the calculated and measured drop in temperature after the end of the magnetic resonance tomography sequence are compared in order to determine the thermal time constant of the component that is characteristic for a general drop in temperature of the component. The time constant can be determined from the falling signal edge, for example with a normal decay term. Moreover the calculated and measured thermal equilibrium can be compared during the magnetic resonance tomography sequence, in order to determine a thermal capacitance of the component. The thermal equilibrium can (approximately) be assumed in the (almost) horizontal temperature waveform. As an alternative the thermal capacitance can also be determined from the rise in the temperature waveform at the beginning. The time constant and the heat constant can for example be determined such that their value is adapted in the temperature model so that the measured and the calculated temperature waveform are approximately identical. In order to be able to determine the thermal equilibrium as accurately as possible, first of all the time constant can be determined, which can then also be included for the determination of the equilibrium. The thermal capacitance can in particular be determined based on the height of the thermal equilibrium and the time constant of the drop in temperature. In a further step 314 the temperature model is adapted with the thermal time constant determined and the thermal capacitance determined. In the simulated temperature waveform of the temperature model the model was already calibrated, so that the measured and the simulated temperature waveform have almost the same shape. The comparison of FIGS. 5 and 6 shows that a temperature waveform can thus be simulated very exactly with the temperature model.

Figure 7:
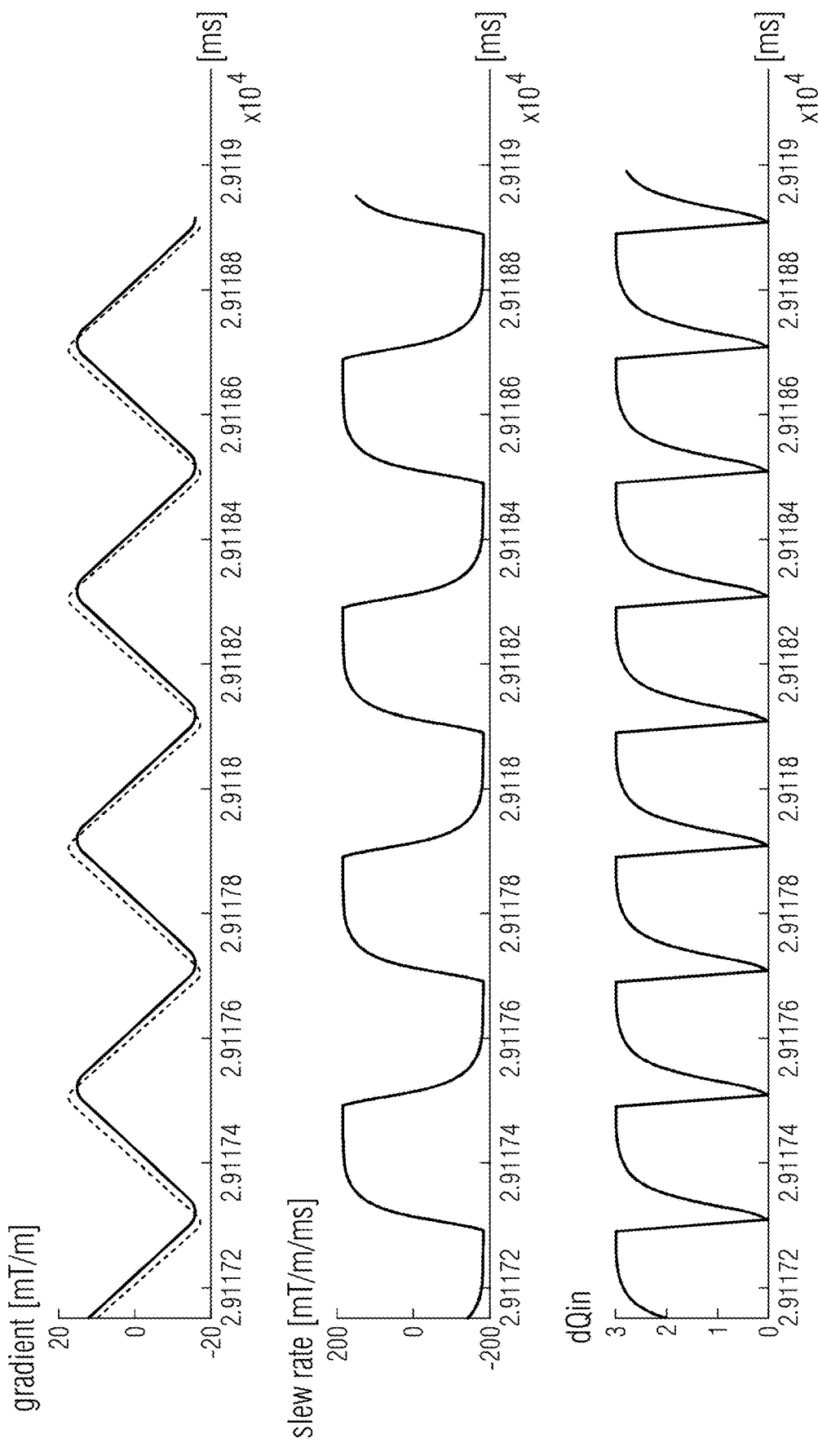
FIG. 7 shows a gradient waveform, an associated curve of the slew rate of a gradient and a curve established therefrom of a heat input of a component

FIG. 7 shows an example of a gradient waveform (top), an associated curve of the slew rate of a gradient (middle) and a curve of a heat input (supply of heat) determined therefrom in a component (bottom). The slew rate can be used, as specified in equation 6 for example, in order to calculate the heat input. Shown in the plot of the gradient waveform is an actual gradient waveform (dashed line) and a gradient waveform, which corresponds to a delay of the gradient waveform caused by induction (solid line). This offset of the actual gradient waveform as well as the gradient waveform set can be determined for example by a simulation and the temperature model can be corrected accordingly with this offset (which stems from the difference between the dashed line and the solid line). For example a time constant of the induced eddy current can be established by a simulation. The time constant can in particular be dependent on geometry and conductivity of the component. The time constant can be inserted into the model in order to thus obtain the actual, delayed "gradient" waveform. This delayed waveform then corresponds in particular to the waveform of the eddy current.

Figure 8:
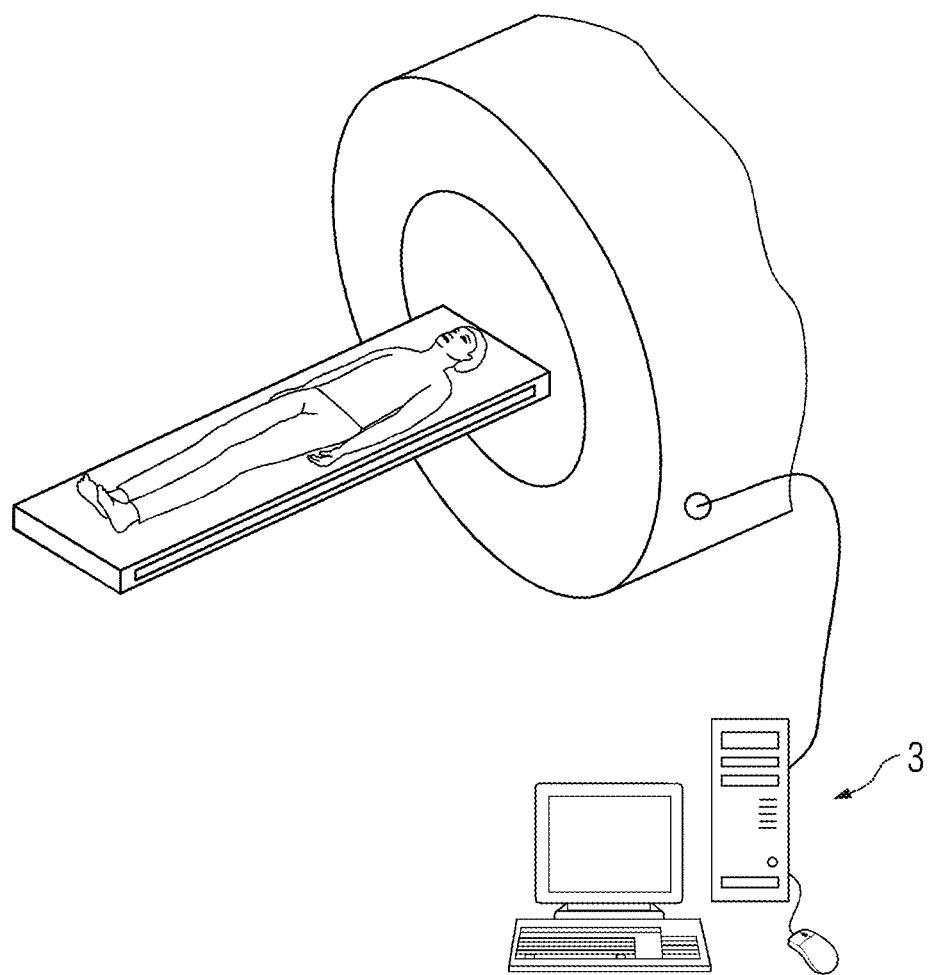
FIG. 8 shows a magnetic resonance tomography system in accordance with one embodiment of the invention.

FIG. 8 shows a magnetic resonance tomography system with a control module 3, which comprises a computer program, which is configured for carrying out an inventive method, as shown in FIG. 1 or in FIG. 3 for example. The magnetic resonance tomography system can comprise a PET system, so that DEA electronics boards as shown in FIG. 3 (hidden here by the outer shell of the examination tunnel) are arranged in the examination tunnel. A few or all of the DEA electronics boards can be the components that will be monitored or protected with the method.

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that encompasses relationship a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particular manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, a and/or combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, similar electronic or computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particular manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The invention claimed is:

1. A computer-implemented method for estimating an influence of a magnetic resonance tomography sequence on at least one component in or on an examination tunnel of a magnetic resonance tomography system, the method comprising:

inputting at least one gradient waveform of the magnetic resonance tomography sequence into a temperature model;

calculating an increase in temperature caused by an application of the magnetic resonance tomography sequence in the at least one component using the temperature model, the temperature model configured to calculate the increase in temperature based on an estimation of eddy currents induced by the at least one gradient waveform in the at least one component, the calculating including, determining at least one radial vector, the at least one radial vector is a characteristic for an induced eddy current and is perpendicular to a surface of the at least one component; and outputting at least one of the calculated increase in temperature or a temperature achieved by the increase in temperature.

2. The method of claim 1, wherein the calculating is further based on at least one amount of heat taken up and at least one amount of heat given out of the at least one component.

3. The method of claim 1, wherein
the calculating is further based on a solution of a differential equation, and
the differential equation relates to a change in temperature of the at least one component and comprises at least one amount of heat.

4. The method of claim 1, wherein
the magnetic resonance tomography system comprises a number of gradient coils, each of the gradient coils associated with the at least one gradient waveform, and
the at least one radial vector includes a radial vector for each of the gradient coils.

5. The method of claim 1, wherein the temperature model comprises at least one characteristic physical constant relating to a temperature waveform of the at least one component.

6. A computer-implemented method for protection of at least one component in or on an examination tunnel of a magnetic resonance tomography system, the method comprising:

receiving a magnetic resonance tomography sequence to be carried out with the magnetic resonance tomography system;

applying the method of claim 1;

checking whether the calculated increase in temperature exceeds a pre-defined temperature threshold; and if the temperature threshold is exceeded, at least one of adapting at least one of the magnetic resonance tomography sequence or outputting to a user a proposal for adapting the magnetic resonance tomography sequence.

7. A non-transitory computer-readable medium comprising instructions for a temperature model, when executed by a system, cause the system to perform the method of claim 1.

8. A magnetic resonance tomography system comprising:
a control module storing instructions to perform the method of claim 1.

9. The method of claim 4, wherein the calculating calculates an amount of heat caused by the induced eddy currents, contributions of gradient fields to an induction voltage are weighted with a respective slew rate of the gradient coils.

10. The method of claim 2, wherein the at least one amount of heat taken up includes heat induced by the eddy currents.

11. The method of claim 4, wherein the number of gradient coils is at least two gradient coils.

12. The method of claim 5, wherein the at least one characteristic physical constant includes at least one of a thermal capacitance constant of the at least one component, a thermal time constant of the at least one component, or a delay in an occurrence of an induced eddy current relative to the at least one gradient waveform.

13. The method of claim 2, wherein
the calculating is further based on a solution of a differential equation, and
the differential equation relates to a change in temperature of the at least one component.

* * * * *